United States Patent
Yamamoto et al.

(10) Patent No.: US 9,102,641 B2
(45) Date of Patent: Aug. 11, 2015

(54) METHOD FOR PRODUCING PROPYLENE OXIDE

(75) Inventors: Jun Yamamoto, Sodegaura (JP); Shigeru Goto, Chiba (JP)

(73) Assignee: SUMITOMO CHEMICAL COMPANY LIMITED, Tokyo (JP)

( * ) Notice: Subject to any disclaimer, the term of this patent is extended or adjusted under 35 U.S.C. 154(b) by 315 days.

(21) Appl. No.: 12/450,316

(22) PCT Filed: Mar. 21, 2008

(86) PCT No.: PCT/JP2008/055986
§ 371 (c)(1),
(2), (4) Date: Sep. 21, 2009

(87) PCT Pub. No.: WO2008/123384
PCT Pub. Date: Oct. 16, 2008

(65) Prior Publication Data
US 2010/0048925 A1 Feb. 25, 2010

(30) Foreign Application Priority Data
Mar. 22, 2007 (JP) ................. 2007-074375

(51) Int. Cl.
*C07D 301/19* (2006.01)
*C07D 301/06* (2006.01)
*C07D 303/04* (2006.01)

(52) U.S. Cl.
CPC ............ *C07D 301/19* (2013.01); *C07D 303/04* (2013.01)

(58) Field of Classification Search
CPC ............................ C07D 303/04; C07D 301/19
USPC .................................................. 549/529, 524
See application file for complete search history.

(56) References Cited

U.S. PATENT DOCUMENTS

| | | | |
|---|---|---|---|
| 6,639,086 B2 | 10/2003 | Tsuji et al. | |
| 7,449,590 B2 | 11/2008 | Tsuji et al. | |
| 7,705,166 B2 * | 4/2010 | Tsuji et al. | 549/529 |

(Continued)

FOREIGN PATENT DOCUMENTS

| | | |
|---|---|---|
| CA | 1 266 052 | 2/1990 |
| EP | 1 266 891 | 12/2002 |

(Continued)

OTHER PUBLICATIONS

Supplementary European Search Report issued Aug. 6, 2010 in corresponding European application No. 08722919.
International Search Report issued Jun. 24, 2008 in International (PCT) Application No. PCT/JP2008/055986.

(Continued)

*Primary Examiner* — Taylor Victor Oh
(74) *Attorney, Agent, or Firm* — Wenderoth, Lind & Ponack, L.L.P.

(57) ABSTRACT

A method for producing propylene oxide in which the concentration of an organic peroxide in a reaction solution after an epoxidation step is from 20 to 5,000 ppm by weight based on the amount excluding propylene in the reaction solution, the method comprising an epoxidation step of reacting an organic peroxide with propylene in the presence of a catalyst to obtain propylene oxide and an alcohol, a propylene recovery step of recovering the unreacted propylene in the epoxidation step and recycling the resulting propylene as a raw material of the epoxidation step, and a propylene oxide purification step of distilling the propylene oxide obtained in the epoxidation step to obtain purified propylene oxide.

18 Claims, 2 Drawing Sheets

(56) References Cited

U.S. PATENT DOCUMENTS

| | | | |
|---|---|---|---|
| 2003/0032822 A1 | 2/2003 | Tsuji et al. | |
| 2004/0127729 A1 | 7/2004 | Oku et al. | |
| 2004/0133018 A1 | 7/2004 | Oku et al. | |
| 2004/0192945 A1 | 9/2004 | Teles et al. | |
| 2004/0254386 A1* | 12/2004 | Tsuji et al. | 549/529 |
| 2005/0070725 A1* | 3/2005 | Ploemen et al. | 549/529 |

FOREIGN PATENT DOCUMENTS

| | | | |
|---|---|---|---|
| EP | 1 437 350 | | 7/2004 |
| JP | 9-169751 | | 6/1997 |
| JP | 2001-270877 | | 10/2001 |
| JP | 2002-322164 | | 11/2002 |
| JP | 2002-322167 | | 11/2002 |
| JP | 2005-97175 | | 4/2005 |
| JP | 2005-97185 | | 4/2005 |
| JP | 2005097175 | * | 4/2005 |
| JP | 2005097185 | * | 4/2005 |
| WO | 00/17178 | | 3/2000 |
| WO | 01/70711 | | 9/2001 |
| WO | 03/027087 | | 4/2003 |
| WO | 2005/030742 | | 7/2004 |

OTHER PUBLICATIONS

PCT Written Opinion issued Jun. 24, 2008 in International (PCT) Application No. PCT/JP2008/055986.

Office Action issued Apr. 13, 2011 in corresponding Chinese patent application No. 200880008733.2, with English translation.

Office Action issued Jul. 6, 2012 in corresponding Chinese patent application No. 200880008733.2, with English translation.

Office Action issued Mar. 29, 2012 issued in corresponding GCC patent application No. GCC/P/2008/10413.

Office Action issued Jan. 21, 2010 in corresponding Singapore patent application No. 200905817-3.

Notice of opposition issued May 14, 2012 in corresponding European patent application No. 08722919.1 (Patent No. 2137174).

Advances in the Technology for Propylene Oxide Production, Ryoji Ishioka, Journal of Synthetic Organic Chemistry, 1978, vol. 36, No. 4, 308-313 (partial translation).

Japanese Office Action issued Jan. 8, 2013, in corresponding application No. 2008-063753 (with English translation).

Office Action dated May 20, 2014, in corresponding Korean Application No. 2009-7021133 (with English translation).

Indian Office Action issued Jun. 30, 2014 in corresponding Indian Application No. 6197/CHENP/2009.

* cited by examiner

METHOD FOR PRODUCING PROPYLENE OXIDE

TECHNICAL FIELD

The present invention relates to a method for producing propylene oxide. More particularly, the present invention relates to a method for producing propylene oxide, comprising a step of reacting an organic peroxide with propylene in the presence of a catalyst to obtain propylene oxide and an alcohol (an epoxidation step); a step of recovering the unreacted propylene in the epoxidation step and recycling the resulting propylene as a raw material of the epoxidation step (a propylene recovery step); and a step of distilling the propylene oxide obtained in the epoxidation step to obtain purified propylene oxide (a propylene oxide purification step). This method has excellent effect capable of efficiently carrying out an epoxidation reaction, and also suppressing loss of a valuable component such as propylene or propylene oxide, and saving energy required to purify propylene oxide.

BACKGROUND ART

Japanese Unexamined Patent Publication (Kokai) No. 2005-097175 discloses, for example, a method for producing propylene oxide, comprising an epoxidation step, a propylene recovery step, and a propylene oxide purification step. Furthermore, Japanese Unexamined Patent Publication (Kokai) No. 2005-097185 discloses a method for producing propylene oxide in which the reaction is carried out at the concentration of cumene hydroperoxide of 2% by weight or less as the concentration of an organic peroxide in a reaction solution upon the completion of the epoxidation step.

However, it was impossible for these conventional methods to efficiently carry out an epoxidation reaction, sufficiently suppress loss of a valuable component such as propylene or propylene oxide, and to sufficiently save energy in a propylene oxide purification step. Thus, a further improvement has been required.

DISCLOSURE OF THE INVENTION

An object to be achieved by the present invention is to provide a method for producing propylene oxide, comprising a step of reacting an organic peroxide with propylene in the presence of a catalyst to obtain propylene oxide and an alcohol (an epoxidation step); a step of recovering the unreacted propylene in the epoxidation step and recycling the resulting propylene as a raw material of the epoxidation step (a propylene recovery step); and a step of distilling the propylene oxide obtained in the epoxidation step to obtain purified propylene oxide (a propylene oxide purification step), the method having excellent effect capable of efficiently carrying out an epoxidation reaction, and also suppressing loss of a valuable component such as propylene or propylene oxide, and saving energy required to purify propylene oxide.

That is, the present invention pertains to a method for producing propylene oxide in which the concentration of an organic peroxide in a reaction solution after an epoxidation step is from 20 to 5,000 ppm by weight (based on the amount excluding propylene in the reaction solution) (this concentration of organic peroxide is sometimes referred to as a "control concentration of an organic peroxide", and when the present invention is carried out, those skilled in the art can appropriately determine upper and lower limits of the concentration within the above range), the method comprising the following steps:

an epoxidation step of reacting an organic peroxide with propylene in the presence of a catalyst to obtain propylene oxide and an alcohol;

a propylene recovery step of recovering the unreacted propylene in the epoxidation step and recycling the resulting propylene as a raw material of the epoxidation step; and a propylene oxide purification step of distilling the propylene oxide obtained in the epoxidation step to obtain purified propylene oxide.

According to the present invention, it is possible to provide a method for producing propylene oxide, comprising a step of reacting an organic peroxide with propylene in the presence of a catalyst to obtain propylene oxide and an alcohol (an epoxidation step); a step of recovering the unreacted propylene in the epoxidation step and recycling the resulting propylene as a raw material of the epoxidation step (a propylene recovery step); and a step of distilling the propylene oxide obtained in the epoxidation step to obtain purified propylene oxide (a propylene oxide purification step), the method having excellent effect capable of efficiently carrying out an epoxidation reaction, and also suppressing loss of a valuable component such as propylene or propylene oxide, and saving energy required to purify propylene oxide.

BRIEF DESCRIPTION OF THE DRAWINGS

In FIG. 1, reference Numerals denotes followings.
(1): oxidization reaction solution
(2): Epoxidation reaction solution
(3): Unreacted propylene
(4): Reaction solution after recovering propylene
(5): Solution mainly containing cumyl alcohol and cumene
(6): Recycle cumene.
In FIG. 2, symbols *1, *2, *3, *4 denotes followings.
*1: Require to confirm effect after changing reaction conditions
*2: Keep same reaction conditions until subsequent analysis
*3: Possible to consider decrease in filling amount of catalyst when reaction temperature is lower than preferable operation temperature for long period of time
*4: Retention time of epoxidation reaction step≤waiting time≤(time interval of periodic analysis=24 hours)

BEST MODE FOR CARRYING OUT THE INVENTION

Figure 1:
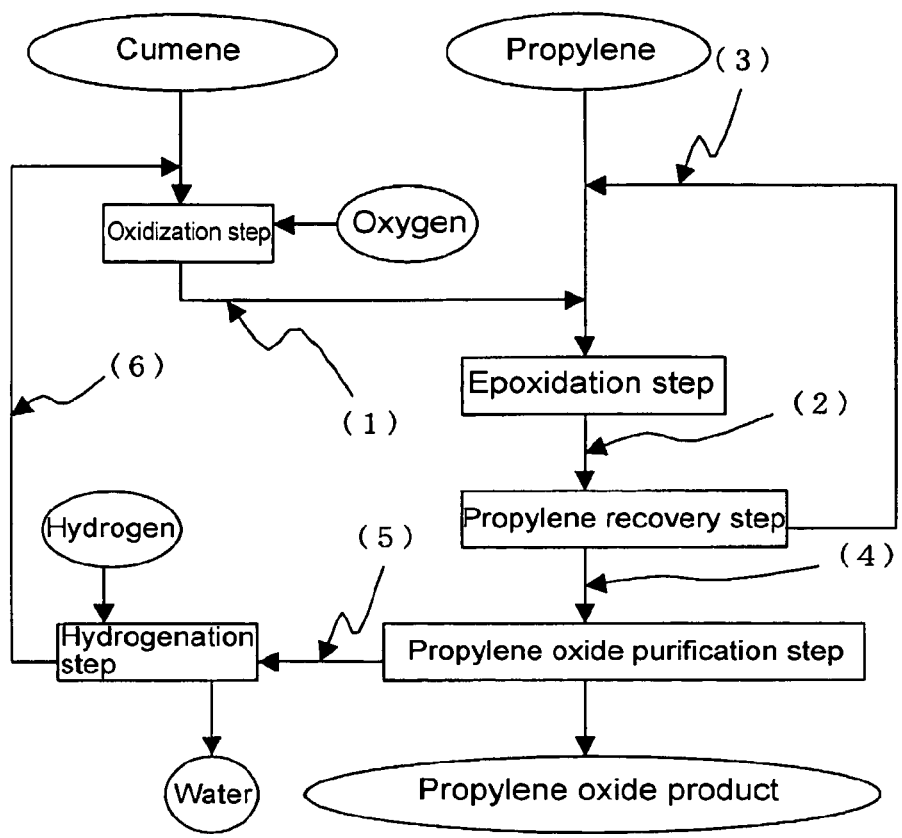
FIG. 1 is a schematic flow chart of Example 1.

The epoxidation step of the present invention is a step of reacting an organic peroxide with propylene in the presence of a catalyst to obtain propylene oxide and an alcohol.

From the viewpoint of obtaining an objective with high yield and high selectivity, the epoxidation step is preferably carried out in the presence of a catalyst composed of a titanium-containing silicon oxide. This catalyst is usually a solid catalyst, and is preferably a so-called Ti-silica catalyst Ti which is chemically bonded with a silicon oxide. The catalyst includes, for example, a catalyst in which a Ti compound is supported on a silica carrier, a catalyst in which a Ti compound is combined with a silicon oxide mixed using a coprecipitation method or a sol gel method, or a catalyst made of a zeolite compound containing Ti.

In the present invention, the organic peroxide used as the raw material of the epoxidation step may be a dilute or concentrated purified material or non-purified material.

The epoxidation reaction is carried out by bringing propylene and an organic peroxide into contact with a catalyst. The reaction is carried out in a liquid phase using a solvent. The solvent must be a liquid under a temperature and a pressure upon the reaction, and must be substantially inactive with a reactant and a product. The solvent may be made of a material which exists in an organic peroxide solution to be used. For example, when ethylbenzene hydroperoxide or cumene hydroperoxide is a mixture containing ethylbenzene and cumene as raw materials thereof, it is possible to use the mixture in place of solvent without adding a solvent. In addition, a useful solvent includes an aromatic monocyclic compound (for example, benzene, toluene, chlorobenzene, or o-dichlorobenzene), and an alkane (octane, decane, or dodecane).

An epoxidation reaction temperature is generally from 0 to 200° C., and is preferably from 25 to 200° C. in view of a reaction rate and economical use of a catalyst, and more preferably from 25 to 140° C. in view of reaction selectivity. When the temperature is too low, the reaction rate is low, and thus the amount of the catalyst, which is required to obtain a desired reaction amount, increases. In contrast, when the temperature is too high, selectivity decreases. Particularly, when the amount of the compound having 4 carbon atoms increases, loss of a valuable component and required energy upon removal of the compound increases. The pressure may be a sufficient pressure to keep a reaction mixture in a liquid state. The pressure is advantageously from 100 to 10,000 kPa.

A solid catalyst is advantageously used in the form of a slurry or a fixed bed. In the case of a large-scale industrial operation, the fixed bed is preferably used. Also, the operation can be carried out by a batch method, a semi-continuous method, or a continuous method. When a liquid containing a reaction raw material is passed through the fixed bed, a liquid mixture from a reacted region does not contain any catalyst, or substantially contains no catalyst.

A mol ratio of propylene/organic peroxide to be supplied to the epoxidation step is preferably from 2/1 to 50/1. When the ratio is too low, the reaction rate decreases, and thus reaction efficiency becomes worse. When the ratio is too high, the amount of propylene to be recycled becomes excessively increases, and thus much energy is required in the recovery step.

The propylene recovery step in the present invention is a step of separating and recovering the unreacted propylene in the epoxidation step and recycling the recovered propylene as a raw material in the epoxidation step. As described above, since propylene is excessively used, the reaction solution from the epoxidation step contains the unreacted propylene. The method of separating and recovering the unreacted propylene from the reaction solution includes a method of distilling the reaction solution. The reaction solution is distilled under the conditions which enable easy evaporation of propylene from the reaction solution. The conditions of distillation vary depending on the temperature and the composition of the reaction solution supplied to the distillation step. Usually, the pressure is from 100 to 5,000 kPa, and preferably from 100 to 3,000 kPa, and a column head temperature is from −50 to 150° C. A method of stepwisely distilling propylene using a plurality of distillation columns can also be used.

The propylene oxide purification step of the present invention is a step of subjecting the propylene oxide produced in the epoxidation step to distillation to obtain purified propylene oxide.

Propylene oxide to be purified is a liquid remained after recovering the unreacted propylene from the reaction solution of the epoxidation step as described above.

Usually, an alcohol and a solvent produced in the epoxidation step are removed by distillation to obtain a crude propylene oxide.

The crude propylene oxide generally contains water, a hydrocarbon, and an oxygen-containing compound as impurities, and the hydrocarbon includes a hydrocarbon having 3 to 7 carbon atoms. Examples of the oxygen-containing compound include methanol, acetaldehyde, acetone, propionaldehyde, and methyl formate.

As the method of removing these impurities, for example, known separation techniques such as distillation, extraction, adsorption, and crystallization may be appropriately used in combination. However, the crude propylene oxide is preferably purified by using extraction distillation with a hydrocarbon having 7 to 10 carbon atoms as an extractant in combination with the other distillation in view of efficiently removing water, a hydrocarbon, and an oxygen-containing compound.

Examples of the hydrocarbon having 7 to 10 carbon atoms as the extractant include linear saturated hydrocarbons such as n-heptanes, n-octane, n-nonane, and n-decane; branched saturated hydrocarbons such as 2,2-dimethylpentane, 2,3-dimethylpentane, 2,2-dimethylhexane, and 2,3-dimethylhexane; and unsaturated hydrocarbons thereof. In addition, these extractants can be used alone, or a mixture thereof can be used.

The model type and operation conditions of an extraction distillation column and other distillation column, an operation condition, and the amount of the extractant are appropriately determined according to the quality of a product to be required.

The purified propylene oxide thus obtained-satisfies desired product quality.

The present invention preferably includes the following epoxidation condition determination steps so as to more accurately control the concentration of the organic peroxide thereby enhancing the effect of the present invention:

an epoxidation condition determination step of measuring the concentration of the organic peroxide in the reaction solution after the epoxidation step and determining necessity of change of conditions of the epoxidation step.

In order to measure the concentration of the organic peroxide in the reaction solution after the epoxidation step, known methods can be used. However, in view of analytical accuracy, an iodine titration method (iodometry), near infrared analysis (NIR), or liquid chromatography (LC) can be used (provided that when a measuring sample contains propylene, it is necessary to correct the measurement results to the concentration excluding propylene.)

More specific example of the method of controlling the concentration of the organic peroxide includes a method in which sampling is carried out at a frequency required for those skilled in the art control the concentration of the organic peroxide in the reaction solution after the epoxidation step within the above concentration range, for example, a frequency of once a day, and the concentration of the unreacted organic peroxide is controlled within the above range by carrying out an operation of decreasing the reaction temperature of the epoxidation reaction step within a range from 0 to 200° C., preferably from 25 to 200° C., and more preferably from 25 to 140° C. (for example, an operation of decreasing the reaction temperature by 1° C.) when the concentration of the organic peroxide is lower than the control concentration of the organic peroxide of the present invention, or by carrying out an operation of increasing the reaction temperature (for example, an operation of increasing the reaction temperature by 1° C.) when the concentration of the organic peroxide is higher than the control concentration of the organic peroxide. It is also possible to use, as another control method, a method in which the latest measured concentration of the organic peroxide is compared with the past measured value and the next concentration of the organic peroxide is estimated from a tendency of an increase in the concentration, and then an operation of the reaction temperature may be preliminarily changed when it is estimated to exceed the range of the control concentration. Furthermore, control accuracy may be enhanced by a technique in which, when activity of the catalyst is stable, a frequency of analysis decreases thereby decreasing the burden of an operator, whereas, when activity of the catalyst decreases thereby increasing a variation width of the concentration of the organic peroxide, a frequency of analysis is increased. When the temperature of the epoxidation reaction is higher than the range of a predetermined operation temperature and the concentration of the organic peroxide is more than the upper limit of the range of the control concentration, it is preferred to partially or completely exchange the catalyst of the epoxidation step in view of reaction selectivity. When the reaction conditions (for example, a temperature) are changed, it is preferred to reanalyze the concentration of the organic peroxide in the reaction solution in a constant state after a lapse of a time considering the retention time of a reactor and to feed back data whether or not the conditions are properly changed so as to maintain the control concentration in the present invention more accurately. The expression "after a lapse of a time considering the retention time" used herein means "after a lapse of a time in which the amount of a liquid contained in the reactor is divided by the amount of a liquid to be supplied per time" when an epoxidation reactor is an extrusion flow reactor (a plug flow reactor), but is actually means "after a lapse of a time in which those skilled in the art can determine that the composition of the reaction solution after changing the conditions becomes a stable value. It is preferred to analyze again at the time which is not longer than the time interval of the plan analysis.

In the epoxidation condition determination step, it is preferable to systematically determine necessity of change of the temperature of the epoxidation reaction and exchange of the catalyst. For example, when an operator carries out sampling of the reaction solution after the epoxidation step and analyzes in a laboratory, if timing of the sampling after changing conditions is too early, change of conditions based on analytical data in a non-stable state is carried out, namely, unnecessary operations such as temperature rise or catalyst exchange is carried out, it causes uneconomical operation. In contrast, if timing is too late, the determination whether or not an action of change of conditions is properly carried out or becomes to be late, and thus there is a possibility that an operation under unsuitable conditions is carried out for a long time. Namely, it is not preferred that timing of sampling after change of conditions is too early or too late. Thus, it is effective to analyze the concentration of the organic peroxide using NIR or LC capable of executing online analysis instead of laboratory analysis. However, it is also necessary that necessary change of conditions or exchange of the catalyst is not carried out taking account of update intervals of analysis data and time loss up to a stable state.

In the present invention, it is necessary to include the following compound having 4 carbon atoms (C4 compound) removing step so as to more efficiently carry out the epoxidation reaction and to suppress loss of a valuable component such as propylene or propylene oxide:

a compound having 4 carbon atoms removing step of removing the compound having 4 carbon atoms out of the system in each of the epoxidation step, the propylene recovery step and the propylene oxide purification step, or at least one position where the respective steps are connected.

The compound having 4 carbon atoms includes a compound contained in raw materials or auxiliary raw materials in a process for production of propylene oxide, and a compound produced by reacting chemical species having one carbon atom, which is derived from an organic peroxide in the epoxidation step and the unreacted propylene recovery step, with the unreacted propylene. Specific examples of the compound include n-butane, isobutane, 1-butene, 2-butene, and isobutylene.

The compound having 4 carbon atoms is recovered together with propylene when the unreacted propylene is recovered, and is recycled to the epoxidation step. When the compound having 4 carbon atoms removing step is absent, since the compound having 4 carbon atoms is an accumulating component, the concentration in the epoxidation step increases and reaction efficiency decreases when recycling of propylene is continued. When propylene oxide is distilled, the pressure of a distillation column may increase as a result of an increase in the concentration of the compound having 4 carbon atoms, thus causing loss of the valuable component such as propylene oxide or propylene upon gas purging for reducing the column pressure.

While a method of removing the compound having 4 carbon atoms is generally used for distillation, other separation techniques can also be used.

The position where the compound having 4 carbon atoms is removed is at least one position in each of the epoxidation step, the propylene recovery step and the propylene oxide purification step, or at least one position where the respective steps are connected.

Specifically, the method of removing the compound having 4 carbon atoms includes a method of removing by providing a distillation column capable of separating the compound having 4 carbon atoms from propylene oxide in the propylene oxide purified step. The concentration of the compound having 4 carbon atoms is preferably from 0.1 to 100 ppm by weight in propylene oxide after distillation in view of balance between product quality and energy required for purification.

The method of removing the compound having 4 carbon atoms further includes a method in which at least a portion of the compound having 4 carbon atoms is distilled together with propylene when the unreacted propylene is recovered and a column head component containing a large amount of propylene is recycled as a raw material of the epoxidation step, and a column base containing a large amount of the compound having 4 carbon atoms is removed out of the system. The concentration of the compound having 4 carbon atoms is preferably 2% or less by weight in propylene to be recycled in view of efficiently carrying out the epoxidation reaction.

As described above, it is more effective to carry out the compound having 4 carbon atoms removing step at least one position in the above described steps, and preferably at both positions. This step is not limited thereto, and an operator may carry out this step at a proper position by a proper method of removing the compound having 4 carbon atoms.

The distillation conditions in the case of removing the compound having 4 carbon atoms by distillation vary depending on the temperature and the composition of a reaction solution to be supplied. The pressure is usually from 100 to 5,000 kPa, and preferably from 100 to 3,000 kPa, and the column head temperature is from −50 to 150° C. A method of stepwisely distilling using a plurality of distillation columns can also be used.

As the organic peroxide of the present invention, for example, an organic peroxide obtained by oxidizing an aliphatic or aromatic hydrocarbon compound can be used. Specific examples thereof include cumene hydroperoxide and ethylbenzene hydroperoxide.

Preferred method of the present invention includes a method comprising the following oxidation step and hydrogenation step:

an oxidation step of oxidizing cumene to obtain cumene hydroperoxide, and a hydrogenation step of hydrogenating cumyl alcohol obtained in the epoxidation step in the presence of a catalyst and recycling the resulting cumene to the oxidation step as a raw material of the oxidation step.

The oxidation step in the present invention is a step of oxidizing cumene to obtain cumene hydroperoxide. Usually, cumene is automatically oxidized using an oxygen-containing gas such as air or oxygen concentrated air. This oxidation reaction may be carried out without using an additive, or may carried out using an additive such as an alkali. The reaction temperature is usually from 50 to 200° C., and the reaction pressure is from an atmospheric pressure to 5 MPa. In the case of an oxidation method using an additive, an alkali reagent to be used is an alkali metal compound such as NaOH or KOH, an alkali earth metal oxide, an alkali metal carbonate such as $Na_2CO_3$, $NaHCO_3$, ammonia, $(NH_4)_3CO_3$, or an alkali metal ammonium carbonate salt.

The hydrogenation step in the present invention is a step of hydrocracking or dehydrating/hydrogenating cumyl alcohol obtained in the epoxidation step in the presence of a catalyst to obtain cumene, and recycling the resulting cumene to the oxidation step as a raw material of the oxidation step. In order to efficiently recycle cumene, this step is preferably carried out by dehydration/hydrogenation.

The dehydration step is a step of supplying cumyl alcohol obtained in the epoxidation step to a dehydration catalyst to obtain α-methyl styrene and water. Examples of catalyst to be used include acids such as sulfuric acid, phosphoric acid, and p-toluenesulfonic acid; and metal oxides such as activated alumina, titania, zirconia, silica-alumina, and zeolite, of which activated alumina is preferable in view of separation from a reaction solution, catalyst life, and selectivity.

The amount of the dehydration catalyst is an enough amount to convert cumyl alcohol. The conversion ratio of cumyl alcohol is preferably 90% or more, and more preferably 98% or more.

The dehydration reaction is carried out by bringing a solution containing cumyl alcohol into contact with the catalyst. However, in a dehydration/hydrogenation method, a hydrogenation reaction is carried out after the dehydration reaction, and thus hydrogen can be fed to the catalyst. The dehydration reaction temperature is generally from 50 to 450° C., and more preferably from 150 to 300° C. The pressure is advantageously from 10 to 10,000 kPa.

The hydrogenation step is a step of supplying α-methyl styrene obtained in the dehydration step to a hydrogenation catalyst, hydrogenating α-methyl styrene thereby converting into cumene, and recycling cumene to the oxidation step as a raw material of the oxidation step.

The hydrogenation catalyst is a catalyst containing metal of the group 10 or 11 in the Periodic Table, and specific examples thereof include nickel, palladium, platinum and copper, of which palladium or copper is preferable in view of suppression of the hydrogenation reaction of an aromatic ring and high yield. Examples of a copper-based catalyst include copper, Raney copper, copper-chromium, copper-zinc, copper-chromium-zinc, copper-silica, and copper-alumina. Examples of a palladium catalyst include palladium-alumina, palladium-silica, and palladium-carbon. These catalysts may be used alone, or a plurality of them may be used in combination. When the hydrogenation catalyst has dehydration ability, the catalyst can be used alone as a dehydration/hydrogenation catalyst.

The amount of the hydrogenation catalyst is an enough amount to convert α-methyl styrene, and the conversion ratio of α-methyl styrene is preferably 98% or more.

The hydrogenation reaction is carried out by bringing a solution containing α-methyl styrene and hydrogen into contact with the catalyst. However, in a dehydration/hydrogenation method, a hydrogenation reaction is carried out after a dehydration reaction. Therefore, the hydrogenation reaction may be carried out after separating water produced in a dehydration reaction through oil-water separation, or may be carried out by supplying water together with α-methyl styrene to the hydrogenation catalyst without separating water.

The amount of hydrogen required to the reaction may be a molar amount which is equivalent to that of α-methyl styrene. A raw material usually contains other components which consume hydrogen, and thus an excessive amount of hydrogen is required. As a partial pressure of hydrogen increases, the reaction proceeds more quickly, and thus a mol ratio of hydrogen/α-methyl styrene is preferably from 1 to 10, and more preferably from 1 to 5. The excessive hydrogen remained after the reaction can be recycled after separating from a reaction solution.

The hydrogenation reaction temperature is generally from 0 to 500° C., and more preferably 30 to 300° C. The pressure is advantageously from 100 to 10,000 kPa.

The rehydration/hydrogenation reaction can be advantageously carried out using a fixed bed. The dehydration reaction and the hydrogenation reaction may be carried out using a separate reactor, or may be carried out using a single reactor. It is preferable that the dehydration catalyst and the hydrogenation catalyst are not filled in a multi-staged reactor, but are filled in a single fixed bed type reactor in view of cost.

The flow of the reactant may be any one of an up flow, a down flow, and a trickle flow.

The largest aspect of the present invention is that the concentration of the organic peroxide in the reaction solution after the epoxidation step is from 20 to 5,000 ppm by weight, and preferably from 50 to 2,000 ppm by weight (based on the amount excluding propylene in the reaction solution).

The present inventors have intensively studied upon determination of determine the concentration range of the present invention, and found, in addition to the fact that the unreacted organic peroxide in the reaction solution after the epoxidation step is thermally decomposed in the following steps to produce undesirable impurities or polymers thereof, the reaction for production of a compound having 4 carbon atoms through the reaction between chemical species having one carbon atom derived from the unreacted propylene and the unreacted propylene, which has conventionally been unknown. Thus, the present inventors have developed an excellent method for producing propylene oxide, capable of remarkably enhancing efficiency of the epoxidation reaction within the range of upper and lower limits of control concentration, which is by far narrower than a conventional technical range, and also suppressing loss of a valuable component such as propylene or propylene oxide, and saving required to purify propylene oxide.

When the lower limit of the concentration is too low, a reaction ratio of the organic peroxide in the epoxidation step must be maintained at a high value, and thus a catalyst is required to have high activity, or the reaction temperature must be increased. In the former case, the catalyst life is substantially shortened and the amount of the catalyst used increases. In the latter case, selectivity of the reaction decreases, resulting in an uneconomical operation.

In contrast, when the upper limit of the concentration is too high, the amount of by-products produced by decomposition of the organic peroxide after the epoxidation step increases thereby increasing a burden in the following propylene purifying step, resulting in an uneconomical operation. Therefore, when the present invention is carried out, those skilled in the art can appropriately determine upper and lower limits of the concentration within the above range.

When the chemical species having one carbon atom derived from the organic peroxide are generated, these species react with the unreacted propylene to produce a large amount of the compound having 4 carbon atoms, and thus much energy is consumed in the step of removing the compound, and loss of a valuable component such as propylene or propylene oxide increases.

Furthermore, when ethylbenzene hydroperoxide or cumene hydroperoxide obtained by oxidizing ethylbenzene or cumene is used as the organic peroxide in the epoxidation reaction, alcohols to be obtained later are hydrogenated to obtain ethylbenzene or cumene, which can be recycled as an oxidation material. However, the unreacted organic peroxide is thermally decomposed in the following steps after the epoxidation step to produce a product which cannot be recycled, thus increasing loss.

By the above reason, it is disadvantageous even if the concentration of the organic peroxide in the reaction solution after the epoxidation step is too high or low.

As described above, the present invention could provide a method for producing propylene oxide having high-level effect, which cannot be achieved by controlling in a known concentration control range, capable of efficiently carrying out the epoxidation reaction, and also suppressing loss of a valuable component such as propylene or propylene oxide, and saving energy required to purify propylene oxide by controlling the concentration of the organic peroxide in the reaction solution after the epoxidation step within a narrower range with high accuracy.

Example 1

According to the method described in the specification, an oxidization reaction solution (1) containing 31% by weight of cumene hydroperoxide was obtained by oxidizing cumene with an oxygen-containing gas (air) in an oxidation step. An epoxidation reaction solution (2) containing mainly propylene oxide, cumyl alcohol, unreacted propylene, and cumene was obtained by passing the oxidization reaction solution and propylene through a reactor filled with a titanium-containing silicon oxide catalyst in an epoxidation step. The unreacted propylene (3) was separated and removed from the resulting reaction solution (2) to obtain a reaction solution (4) after recovering propylene. The reaction solution (4) after recovering propylene was used in the following Example 3 and Comparative Example 1.

First, the reaction solution (4) after recovering propylene was separated into a fraction of a solution (5) containing mainly cumyl alcohol and cumene and a fraction containing mainly propylene oxide in a propylene oxide purification step, and then the fraction containing mainly propylene oxide was distilled with a plurality of distillation columns including extraction and distillation so as to satisfy product quality to obtain a propylene oxide product. Regarding the fraction of the solution (5) containing mainly cumyl alcohol and cumene, cumyl alcohol was subjected to a dehydration reaction and a hydrogenation reaction in a hydrogenation step to obtain cumene, which was recycled to the oxidization step.

FIG. 1 is a schematic flow chart described in the specification.

Example 2

Figure 2:
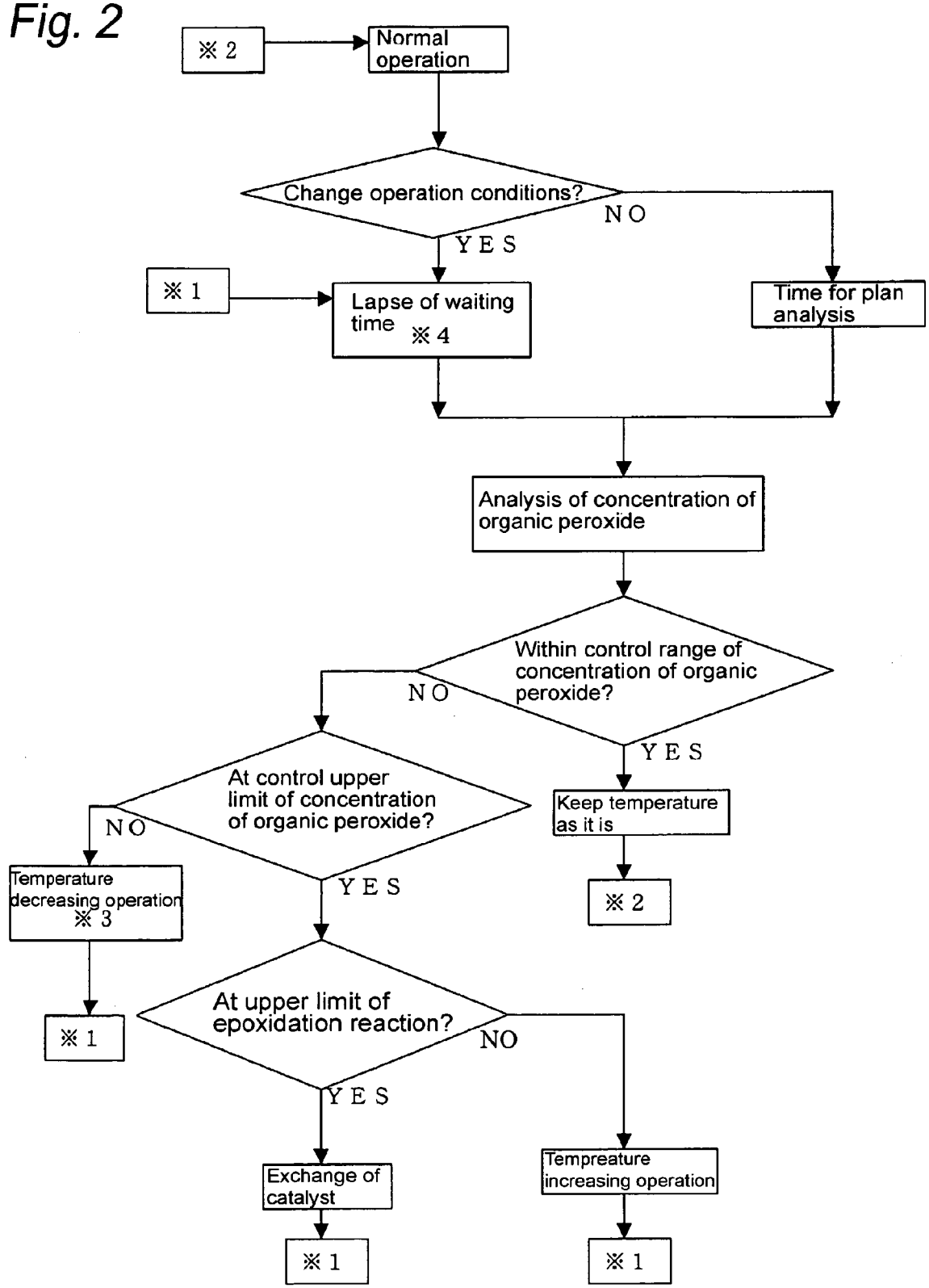
FIG. 2 is a schematic flow chart of Example 2.

FIG. 2 is a flow chart showing a concept of an epoxidation condition determination step described in the specification.

Thus, it is possible to enhance the accuracy of control of the concentration of an organic peroxide in the epoxidation reaction solution (2).

Example 3

In order to confirm the effect of the present invention, the amount of a compound having 4 carbon atoms produced was inspected by the following method.

The compound having 4 carbon atoms is recovered and accumulated together with propylene when the unreacted propylene is recovered and, therefore, purity of propylene used in the epoxidation step decreases and effective epoxidation reaction is prevented, and loss of a valuable component such as propylene or propylene oxide occurs when removed out of the system.

60 g of the reaction solution (4) (containing 8.6% by weight of propylene oxide, 26.7% by weight of cumyl alcohol, and 55.5% by weight of cumene, and containing no propylene) after recovering propylene in Example 1, which contains 0.2% by weight (2,000 ppm by weight) of cumene hydroperoxide, and 33 g of propylene which does not substantially the compound having 4 carbon atoms were charged in a 200 ml autoclave, and then heated at 150° C. for 4 hours (containing a temperature increasing time) under an autogenous pressure. After cooling to 80° C. and depressurization, the gas generated was completely recovered and analyzed by gas chromatography. The concentration of the compound having 4 carbon atoms in the recovered gas was 0.006% by volume. The reaction solution after depressurization contained no cumene hydroperoxide.

Example 4

In order to confirm the effect of the present invention, a relation between the concentration of the compound having 4 carbon atoms and energy required to purify propylene oxide was inspected by the following method.

Main components of the reaction solution after depressurization in Example 3 were analyzed. The results are as shown in Table 1.

TABLE 1

| Components | Concentration (% by weight) | Boiling point (° C.) |
| --- | --- | --- |
| Compound having 4 carbon atoms | 0.001 | −12 to 4 |
| Propylene oxide | 4.0 | 35 |
| Cumene | 57.5 | 152 |
| Cumyl alcohol | 26.9 | 202 |

Example 5

The same operation as in Example 3 was carried out, except for using the reaction solution (4) after recovering propylene described in Example 1, which contains 0.5% by weight (5,000 ppm by weight) of cumene hydroperoxide. The concentration of the compound having 4 carbon atoms in the recovered gas was 0.014% by volume. The reaction solution after depressurization contained no cumene hydroperoxide.

Example 6

Main components of the reaction solution after depressurization in Example 5 were analyzed. The results are as shown in Table 2.

TABLE 2

| Components | Concentration (% by weight) | Boiling point (° C.) |
|---|---|---|
| Compound having 4 carbon atoms | 0.002 | −12 to 4 |
| Propylene oxide | 5.2 | 35 |
| Cumene | 55.2 | 152 |
| Cumyl alcohol | 27.4 | 202 |

Comparative Example 1

The same operation as in Example 3 was carried out, except for using the reaction solution (4) after recovering propylene described in Example 1, which contains 2.0% by weight of cumene hydroperoxide. The concentration of the compound having 4 carbon atom in the recovered gas was 0.074% by volume. Further, the concentration of cumene hydroperoxide in the reaction solution after depressurization was 0.02% by weight. As a result, it was found that the amount of the compound having 4 carbon atoms generated is more than that of Example 3 or 5, and thus loss of a valuable component such as propylene oxide or propylene of Comparative Example 1 in the propylene recovering step of the present invention is more than that of Example 3 or 5.

Comparative Example 2

Main components of the reaction solution after depressurization in Comparative Example 1 were analyzed. The results are as shown in Table 3.

TABLE 3

| Components | Concentration (% by weight) | Boiling point (° C.) |
|---|---|---|
| Compound having 4 carbon atoms | 0.005 | −12 to 4 |
| Propylene oxide | 4.8 | 35 |
| Cumene | 56.1 | 152 |
| Cumyl alcohol | 28.1 | 202 |

A boiling point of each component was shown in Example 4, 6 and Comparative Example 2. It is found that the compound having 4 carbon atoms is a light boiling compound whose boiling point is comparatively close to that of propylene oxide, and thus rectification is required to separate propylene oxide. A comparison between Table 1, 2 and Table 3 revealed that energy required to separate the compound having 4 carbon atoms from propylene oxide in the propylene oxide purifying step in Comparative Example 2 is more than that in Example 4 or Example 6.

The invention claimed is:

1. A method for producing propylene oxide in which the concentration of an organic peroxide in a reaction solution after an epoxidation step is from 20 to 5,000 ppm by weight based on the amount excluding propylene in the reaction solution, the method comprising the following steps:
    an epoxidation step of reacting an organic peroxide with propylene in the presence of a catalyst composed of a titanium-containing silicon oxide to obtain a reaction mixture comprising propylene oxide and an alcohol;
    a propylene recovery step of separating and recovering the unreacted propylene from the reaction mixture produced in the epoxidation step and recycling the resulting propylene as a raw material of the epoxidation step; and
    a propylene oxide purification step of distilling the propylene oxide obtained in the epoxidation step to obtain purified propylene oxide,
    wherein the method is performed in a system, and
    wherein the method further comprises the following step:
    a compound having 4 carbon atoms removing step of removing the compound having 4 carbon atoms out of the system at at least one in each of the epoxidation step, the propylene recovery step and the propylene oxide purification step, or at at least one position where the respective steps are connected.

2. The method for producing propylene oxide according to claim 1, wherein the concentration of the organic peroxide in the reaction solution after the epoxidation step is from 50 to 2,000 ppm by weight based on the amount excluding propylene in the reaction solution.

3. The method for producing propylene oxide according to claim 1, further comprising the following step:
    an epoxidation condition determination step of measuring the concentration of the organic peroxide in the reaction solution after the epoxidation step and determining necessity of change of conditions of the epoxidation step.

4. The method for producing propylene oxide according to claim 1, wherein one or more distillation columns in the propylene oxide purification step are used at at least one position of the compound having 4 carbon atoms removing step and the concentration of the compound having 4 carbon atoms in propylene oxide after distillation is from 0.1 to 100 ppm by weight.

5. The method for producing propylene oxide according to claim 1, wherein one or more distillation columns disposed at the position where the propylene recovery step is connected with the epoxidation step are used at at least one position of the compound having 4 carbon atoms removing step and the concentration of the compound having 4 carbon atoms in propylene used in the epoxidation step is 2% by weight or less.

6. The method for producing propylene oxide according to claim 1, wherein main organic peroxide is ethylbenzene hydroperoxide.

7. The method for producing propylene oxide according to claim 1, wherein main organic peroxide is cumene hydroperoxide.

8. The method for producing propylene oxide according to claim 7, further comprising the following steps:
    an oxidation step of oxidizing cumene to obtain cumene hydroperoxide; and
    a dehydration/hydrogenation step comprising supplying cumyl alcohol obtained in the epoxidation step to a dehydration catalyst selected from the group consisting of sulfuric acid, phosphoric acid, p-toluenesulfonic acid, activated alumina, titania, zirconia, silica-alumina and zeolite to obtain α-methylstyrene and water; hydrogenating the α-methylstyrene by using a hydrogenation catalyst containing a metal of group 10 or 11 in the Periodic Table to obtain cumene; and recycling the resulting cumene to the oxidation step as a raw material of the oxidation step.

9. The method for producing propylene oxide according to claim 2, further comprising the following step:
    an epoxidation condition determination step of measuring the concentration of the organic peroxide in the reaction solution after the epoxidation step and determining necessity of change of conditions of the epoxidation step.

10. The method for producing propylene oxide according to claim 4, wherein one or more distillation columns disposed at the position where the propylene recovery step is connected with the epoxidation step are used at at least one position of the compound having 4 carbon atoms removing step and the concentration of the compound having 4 carbon atoms in propylene used in the epoxidation step is 2% by weight or less.

11. The method for producing propylene oxide according to claim 2, wherein main organic peroxide is ethylbenzene hydroperoxide.

12. The method for producing propylene oxide according to claim 3, wherein main organic peroxide is ethylbenzene hydroperoxide.

13. The method for producing propylene oxide according to claim 5, wherein main organic peroxide is ethylbenzene hydroperoxide.

14. The method for producing propylene oxide according to claim 2, wherein main organic peroxide is cumene hydroperoxide.

15. The method for producing propylene oxide according to claim 3, wherein main organic peroxide is cumene hydroperoxide.

16. The method for producing propylene oxide according to claim 4, wherein main organic peroxide is cumene hydroperoxide.

17. The method for producing propylene oxide according to claim 5, wherein main organic peroxide is cumene hydroperoxide.

18. The method for producing propylene oxide according to claim 8, wherein the metal of group 10 or 11 in the Periodic Table is selected from the group consisting of nickel, palladium, platinum and copper.

* * * * *